United States Patent [19]

Kraushaar-Czarnetzki et al.

[11] Patent Number: 5,294,739
[45] Date of Patent: Mar. 15, 1994

[54] CATALYTIC OXIDATION OF HYDROCARBONS

[75] Inventors: Bettina Kraushaar-Czarnetzki; Willemina G. M. Hoogervorst, both of Amsterdam, Netherlands

[73] Assignee: Shell Oil Company, Houston, Tex.

[21] Appl. No.: 897,151

[22] Filed: Jun. 11, 1992

[30] Foreign Application Priority Data

Jun. 20, 1991 [GB] United Kingdom ............... 9113343

[51] Int. Cl.$^5$ .................... C07C 15/10; C07C 27/12; C07C 45/33; C07C 29/50
[52] U.S. Cl. .................................. 562/543; 562/568; 502/74; 502/152
[58] Field of Search ............... 562/543, 568; 502/150, 502/152, 11, 74

[56] References Cited

U.S. PATENT DOCUMENTS

| | | | |
|---|---|---|---|
| 3,529,020 | 9/1970 | Landis | 260/524 |
| 3,926,845 | 12/1975 | Cichowski | 252/432 |
| 4,341,907 | 7/1982 | Zelonka | 568/360 |
| 4,410,464 | 10/1983 | Hallgren | 558/274 X |
| 4,567,029 | 1/1986 | Wilson et al. | 423/306 |
| 4,658,056 | 4/1987 | Sipos | 562/523 |
| 4,952,384 | 8/1990 | Lok et al. | 423/306 |

FOREIGN PATENT DOCUMENTS

| | | |
|---|---|---|
| 0158350 | 10/1985 | European Pat. Off. |
| 0161489 | 11/1985 | European Pat. Off. |
| 92201779 | 1/1993 | European Pat. Off. |
| 3733782A | 4/1989 | Fed. Rep. of Germany |
| 8021642 | 2/1983 | Japan |
| 3303936A | 12/1988 | Japan |
| 1294646A | 11/1989 | Japan |

OTHER PUBLICATIONS

J. M. Bennett and B. K. Marcus, "Innovation in Zeolite Materials Science" (Eds. P. J. Grobet et al.), Series: *Studies in Surface Science and Catalysis*, vol. 37, Elsevier, Amsterdam (1988), pp. 269-279.

"New Developments in Zeolite Science Technology," (Eds. Y. Murakami, A. Lijima and J. W. Ward), *Stud. Surf. Sci. Catal.*, vol. 28, Elsevier, Tokyo (1986), pp. 103-111.

*Primary Examiner*—Arthur C. Prescott

[57] ABSTRACT

The invention relates to a process for the catalytic oxidation of hydrocarbons with molecular oxygen using a cobalt-containing molecular sieve material having the cobalt ions substantially incorporated in the crystal lattice of the molecular sieve. Preferably, the oxidation is carried out with a molecular sieve containing from about 0.1% to about 10% by weight of cobalt and wherein the cobalt ions are substantially trivalent when the reaction starts. Preferably, the catalyst is a cobalt containing phosphate based molecular sieve material of the structure type 5, 31, 36, 37, 40, 50 and mixtures thereof and the hydrocarbons oxidized are from the group consisting of straight chain alkanes, alkenes, cycloalkanes and cycloalkenes which contain from about 3 to about 20 carbon atoms.

17 Claims, No Drawings

CATALYTIC OXIDATION OF HYDROCARBONS

BACKGROUND OF THE INVENTION

1. Field of the Invention

The present invention relates to a chemical process for the catalytic oxidation of hydrocarbons with molecular oxygen utilizing a cobalt-containing catalyst.

2. Description of the Prior Art

Hydrocarbon oxidation products in large quantities are valuable products for chemically processing polyamides, polyesters or fuel enhancers. Processes for the catalytic oxidation of hydrocarbons with molecular oxygen using a cobalt-containing catalyst are known in the art. DE-A-3 733 782 (Zakladi -0 Azotowe lip.) discloses a process for oxidizing cyclohexane to cyclohexanol and cyclohexanone with molecular oxygen under pressure at a temperature between 150° C. to 200° C. using cobalt naphthenate as a catalyst. JP-A-01 294 646 (Mitsubishi Kasei Corp.) discloses a process for the oxidation of cyclohexane to cyclohexanol and cyclohexanone with molecular oxygen in the presence of, among other things, a magnesium double oxide containing cobalt such as Mg-Al-hydrotalcite, $MGO-Al_2O_3$ or a zeolite ion exchanged with $Mg^{2+}$ and optionally cobalt ions at a reaction temperature and pressure of from 110° C. to 180° C. and below 100 kg/cm² respectively. In a similar oxidation reaction, JP-A-3 303 936 discloses tile use of a certain phyllosilicate catalysts in which cations have been exchanged with cobalt ions.

There are numerous disadvantages associated with the prior art processes. After the oxidation reaction, the cobalt ions must be recovered from the reaction liquid. Cobalt ions introduced into a molecular sieve by cation exchange are present on the surface of the ion exchange material where they are loosely attached, mainly by electrostatic forces. These ions are easily leached out during the oxidation reaction thereby contaminating the reaction product. In addition, the catalytic activity of the molecular sieve is decreased. The actual catalysis may in fact be due to the cobalt ions in solution.

Reaction temperatures in the range of from 150° C. and 200° C. are also considered a disadvantage since they are relatively high and tend to produce reaction products of a darker color. In addition, these reaction temperatures induce chain length degradation in the reaction products.

Because of these disadvantages, there currently exists a need for an economically attractive industrial bulk manufacturing process utilizing cheap hydrocarbon starting materials and operating under attractive, safe, economical and environmental conditions.

SUMMARY OF THE INVENTION

The present invention relates to a process for the catalytic oxidation of hydrocarbons wherein the hydrocarbons are contacted with a source of molecular oxygen and a cobalt-containing catalyst wherein the cobalt-containing catalyst is a molecular sieve material comprising a crystal lattice having cobalt ions incorporated in the crystal lattice.

DESCRIPTION OF THE PREFERRED EMBODIMENTS

In the process of the present invention, hydrocarbons are oxidized with molecular oxygen using a cobalt-containing catalyst which is a molecular sieve material having the cobalt ions incorporated in the crystal lattice of the molecular sieve. By using such a catalytic material, the active cobalt ions which are well integrated in the crystal lattice are permanently fixed. As a consequence, the ions retain their position in the crystal lattice during the oxidation reaction thereby preventing any appreciable decrease in catalytic activity and contamination of the reaction product by cobalt ions.

In a preferred embodiment of the present invention, the oxidation reaction is started with a molecular sieve material in which the cobalt ions are substantially trivalent. It is, however, possible to use molecular sieve material containing mainly divalent cobalt ions since part of these ions can readily be oxidized to trivalent cobalt ions in situ.

It is recommended to use cobalt containing phosphate based molecular sieve material of the structure type 5, 31, 36, 37, 40 and/or 50 as defined in "New developments in Zeolite Science and Technology", (Eds. Y. Murakamami, A. Lijima and J.W. Ward), Stud. Surf. Sci. Catal., Vol. 28, Elsevier, Tokyo, 1986pp. 103-111 and J. M. Bennett and B. K. Marcuse in "Innovation In Zeolite Material Science", (Eds. P. J. Grobet et al), Series: Studies on Surface Science and Catalysis, Vol. 37, Elsevier, Amsterdam (1988) p. 269 ff, incorporated herein by reference. It is particularly recommended to use a molecular sieve of the class comprising: Co-containing MeAPO's (as described as CoAPO's in U.S. Pat. No. 4,567,029); Co-containing MeAPSO's (as described as CoAPSO's in EP-A-161 489); Co-containing XAPO's (as described as FeTiCoAPO's in U.S. Pat. No. 4,952,384); and Co-containing SENAPO's (as described in EP-A-158 350), each incorporated herein by reference.

CoAPO-5molecular sieve materials and similar cobalt aluminophosphate species are very useful in the oxidation reaction. CoAPO-5 and similar molecular sieves and processes for their preparation are described in U.S. Pat. No. 4,567,029 (Union Carbide Corporation), in particular in examples 89-92. This reference is incorporated herein by reference.

Preferably, the molecular sieve utilized does not contain a template, for example, it is in the calcined form. The pore diameter of the molecular sieve is dependent upon the hydrocarbons being oxidized. The diameter should be sufficient large to allow for the adsorption of the hydrocarbons in order to minimize transport problems. For example, in the case of cyclohexane, a pore diameter of at least about 0.65 nanometers is recommended, whereas for the oxidation of straight chain hydrocarbons, a molecular sieve with a pore diameter of at least about 0.38 nanometers is recommended.

The molecular sieve material should contain from about 0.1% to about 10% by weight of cobalt in the lattice. When batchwise oxidation processes are utilized, the amount of cobalt-containing molecular sieve material should range from about 0.5% to about 25% by weight, preferably from about 1% to about 10% by weight, calculated on the basis of the amount of hydrocarbons to be oxidized. In the case of continuous processing, the amount of molecular sieve material used can be lower than that utilized in batchwise oxidation processes.

The oxidation is carried out in the presence of a source of molecular oxygen such as air or oxygen, with the preferred source being air.

It is preferred to carry out the oxidation at a temperature from about 100° C. to about 140° C., more preferably from about 80° C. to about 120° C. The oxygen partial pressure should range from about 100 KPa to about 1000 KPa, more preferably from about 400 KPa to about 800 KPa.

It is often preferred to employ a promoter during the oxidation reaction in order to effectuate a more convenient processing. Inorganic acids, such as phosphoric acid and carboxylic acids, optionally chlorinated or fluorinated, can be used. Lower carboxylic acids (from two to six carbons), such as acetic acid, propanoic acid and butanoic acid are preferred, with acetic acid being the most preferred.

The process according to the present invention can be carried out batchwise, semi-continuously (e.g., cascade method) or continuously, preferably by passing the hydrocarbon to be oxidized in the presence of molecular oxygen over a fluidized bed of cobalt-containing molecular sieve material, in a suitable reactor. This process permits prolonged use of the catalyst bed, which functions as a true heterogenous catalyst because the trivalent cobalt ions remain in the crystal lattice of the molecular sieve during oxidation and thereafter. In addition, there is less contaminated reaction product than known for cobalt catalyzed oxidation reactions up to this time. Regeneration of the catalyst can be achieved easily by calcination.

A multitude of diverse hydrocarbons can be oxidized utilizing the process of the present invention. The process is particularly useful to oxidize hydrocarbons such as straight chain alkanes, alkenes, cycloalkanes and cycloalkenes which contain from about 3 to about 20 carbon atoms.

The products of the oxidation comprise alcohols, aldehydes, ketones and carboxylic acids. The oxidation is non-degrading so the original carbon chain length is for the most part retained. For example, when the preferred starting material cyclohexane is oxidized, the reaction product consists predominantly of cyclohexanol, cyclohexanone and adipic acid with cyclohexylacetate being present in cases where acetic acid is present during the oxidation.

The process of the present invention is further described in the following examples which are provided for illustrative purposes only and are not to be construed as limiting the invention.

ILLUSTRATIVE EMBODIMENT

A mixture comprising 40 ml (31.13 g) of cyclohexane and 10 ml (10.5 g) of acetic acid was transferred to a 500 ml Teflon-lined autoclave. Five grams of CoAPO-5, containing 1.9% by weight Co and having an anhydrous composition which could be expressed in molar oxide ratios as $[0.08\ CoO \cdot 0.99\ Al_2O_3 \cdot 1\ P_2O_5]$ and which previously had been calcined for 2 hours at 550° C., were added. The reaction was performed while the slurry was continuously stirred, applying a pressure (air, containing 21 vol% of oxygen) of $6.5 \times 10^5$ Pa and a temperature of 373° K. After 3 hours, the autoclave was cooled, and the solid catalyst was separated from the liquid by filtration. The liquid was found to contain 4.1 g of the acetic acid ester of cyclohexanol, 2 g of cyclohexanone, 0.1 g of adipic acid and 0.9 g of other oxygenates derived from cyclohexane, among which some degradation products (e.g., n-pentylacetate and n-butylacetate) were found.

After the reaction, investigation of the catalyst showed that both crystallinity and composition were not effected by the oxidation of cyclohexane and that the catalyst had retained its activity. Consequently, no cobalt had leached into the liquid phase.

COMPARATIVE EMBODIMENT

The procedure described above in Example 1 was repeated using as a catalyst template-free SAPO-5 having an anhydrous composition expressed in molar oxide ratios of $[0.21\ SiO_2 \cdot 1 Al_2O_3 \cdot 0.88\ P_2O_5]$ and loaded with 2.6% by weight of cobalt by pore volume impregnation with an aqueous cobalt acetate solution. The product mixture was found to contain 0.9 g of acetic acid ester of cyclohexanol, 0.75 g of cyclohexanone, 0.1 g of adipic acid and 1.1 g of other oxygenates derived from cyclohexane, including degradation products.

After the reaction, the catalyst contained 0.2% by weight of cobalt due to leaching and dissolution in the liquid reaction product.

What is claimed is:

1. A process for the catalytic oxidation of hydrocarbons to produce products comprising alcohols, aldehydes, ketones and carboxylic acids wherein the hydrocarbons are contacts with a source of molecular oxygen and a cobalt-containing catalyst wherein the cobalt-containing catalyst is a molecular sieve material comprising a crystal lattice having cobalt ions incorporated in the crystal lattice.

2. The process of claim I wherein the molecular sieve contains from about 0.1% to about 10% by weight of cobalt ions.

3. The process of claim 2 wherein the amount of cobalt containing molecular sieve material utilized ranges from about 0.5% to about 25% by weight on the basis of the amount of hydrocarbons being oxidized.

4. The process of claim 3 wherein the hydrocarbons oxidized are selected from the group consisting of alkanes, alkenes, cycloalkanes and cycloalkenes which contain from about 3 to about 20 carbon atoms.

5. The process of claim 3 wherein the hydrocarbon being oxidized are cyclohexane.

6. The process of claim 1 wherein the catalyst is a cobalt-containing phosphate based molecular sieve material selected from the group consisting of structure type 5, 31, 36, 37, 40, 50 and mixtures thereof.

7. The process of claim 2 wherein the oxidation is carried at a temperature from about 10° C. to about 1400° C.

8. The process of claim 7 wherein the oxidation is carried out at an oxygen partial pressure from about 100 KPa to about 1000 KPa.

9. The process of claim 2 wherein the oxidation is carried out in the presence of a promoter.

10. The process of claim 9 wherein the promoter is a carboxylic acid having from about two to about six carbons.

11. The process of claim 2 wherein the cobalt ions are substantially trivalent at the start of the reaction.

12. The process of claim 11 wherein the amount of cobalt containing molecular sieve material utilized ranges from about 0.5% to about 25% by weight on the basis of the amount of hydrocarbons being oxidized.

13. The process of claim 12 wherein the oxidation is carried out in the presence of a promoter.

14. The process of claim 13 wherein the promoter is a carboxylic acid having from about two to about six carbons.

15. The process of claim 1 wherein the source of molecular oxygen is air.

16. The process of claim 1 wherein the oxidation is carried out by passing the hydrocarbons in the presence of molecular oxygen over a fluidized bed of cobalt-containing molecular sieve material.

17. A process for the catalytic oxidation of hydrocarbons to produce products comprising alcohols, aldehydes, ketones and carboxylic acids wherein the hydrocarbons are contacted with air and a cobalt-containing catalyst at a temperature from about 10° C. to about 140° C. and an oxygen partial pressure from about 100 KPa to about 1000 KPa, wherein the cobalt-containing catalyst is a molecular sieve material comprising a catalyst lattice having from about 0.1% to about 10% by weight of trivalent cobalt ions substantially incorporated in the crystal lattice and wherein the amount of cobalt-containing molecular sieve material utilized ranges from about 0.5% to about 25% by weight on the basis of the amount of hydrocarbons being oxidized.

* * * * *